United States Patent [19]

Hartley

[11] 4,072,349
[45] Feb. 7, 1978

[54] STEERING OF MINING MACHINES

[75] Inventor: Dennis Hartley, Burton-on-Trent, England

[73] Assignee: Coal Industry (Patents) Limited, London, England

[21] Appl. No.: 687,761

[22] Filed: May 19, 1976

Related U.S. Application Data

[63] Continuation of Ser. No. 525,095, Nov. 19, 1974, abandoned.

[30] Foreign Application Priority Data

Dec. 7, 1973 United Kingdom ............... 56746/73

[51] Int. Cl.² ............................................ E21C 35/08
[52] U.S. Cl. ....................................................... 299/1
[58] Field of Search ................................................ 299/1

[56] References Cited

U.S. PATENT DOCUMENTS

| 3,019,338 | 1/1962 | Monaghan et al. | 299/1 X |
| 3,578,807 | 5/1971 | Barrett | 299/1 |
| 3,674,094 | 7/1972 | Kuntz | 299/1 X |
| 3,719,394 | 3/1973 | Hartley | 299/1 |
| 3,817,578 | 6/1974 | Wilson | 299/1 |

FOREIGN PATENT DOCUMENTS 1,203,362  8/1970  United Kingdom ................. 299/1

Primary Examiner—Ernest R. Purser
Attorney, Agent, or Firm—Stevens, Davis, Miller & Mosher

[57] ABSTRACT

A mineral mining machine which wins a strip of mineral by separate roof and floor cutting stages comprises steering apparatus which senses the cutting horizon associated with one cutting stage to control the cutting horizon associated with the other cutting stage.

18 Claims, 8 Drawing Figures

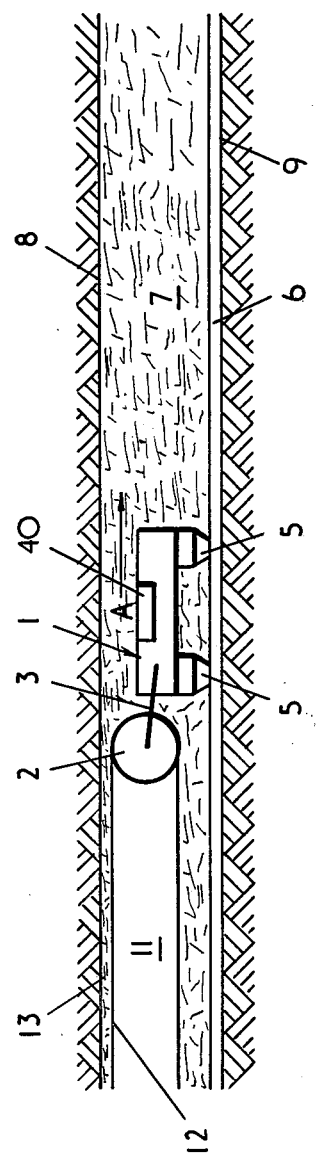
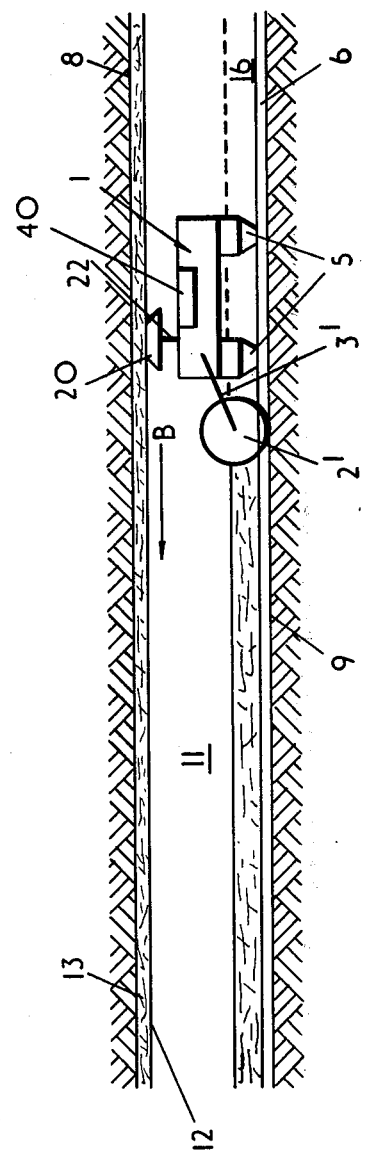

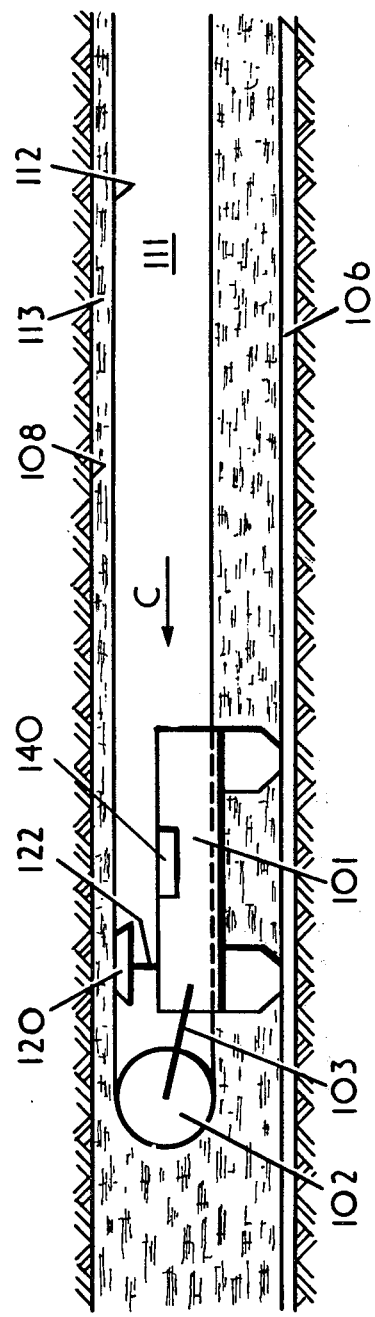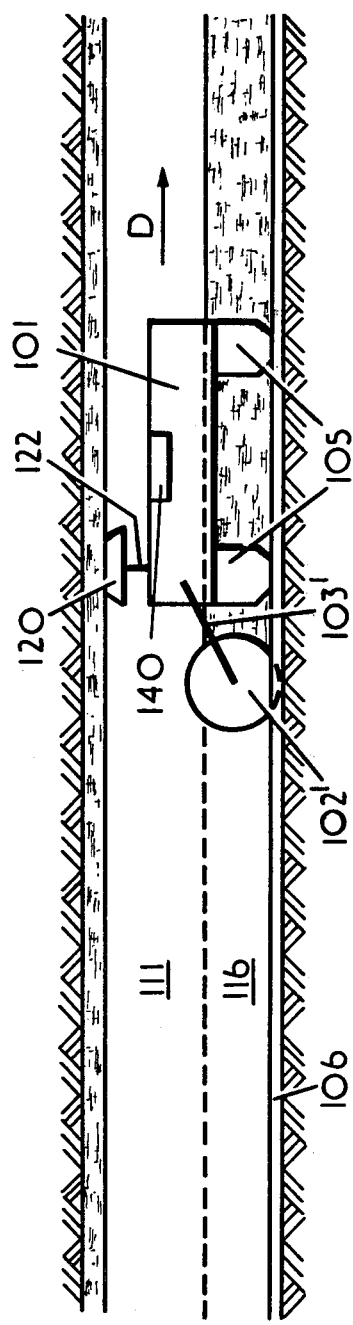

STEERING OF MINING MACHINES

This is a continuation of application Ser. No. 525,095 abandoned filed Nov. 19, 1974.

The present invention relates to steering of mining machines along working faces in underground mineral seams.

In particular the invention relates to steering of mining machines, as for example, ranging drum shearers, which win a strip of mineral by separate roof and floor cutting stages. The machine may comprise a single rotary cutter drum which is mounted on a ranging arm extending from the machine body and which wins mineral adjacent the mine roof, i.e. the roof cutting stage, during one pass along the working face and wins mineral adjacent the mine floor, i.e. the floor cutting stage, during another pass along the working face, the two passes usually being in opposite directions. Alternatively, the machine may comprise two rotary cutter drums which are mounted on ranging arms extending from opposite ends of the machine body, respectively, and which are arranged to win mineral by separate roof and floor cutting stages, respectively, during a single pass of the machine along the working face. This is achieved by having one cutter drum raised to the mine roof and the other cutter drum lowered to the mine floor.

With prior known ranging drum shearers the cutter drums are raised or lowered to steer the machine by operators who have to estimate the cutting horizons of the cutter drums. As the operators are remote from the cutter drums which are surrounded by dust generated during cutting, the steering is often erratic resulting in roof and/or floor rock being mined or in an excessive amount of coal being left unmined.

Methods have been proposed for steering mining machines which have fixed rotary cutter drums, i.e. the position of the axis of the cutter drum is fixed with respect to the body of the machine. With such fixed cutter drum machines the mine roof and floor are formed by one cutting stage and are a fixed distance apart equal to the diameter of the cutter drum. Thus, if the position of the mine roof is known then the position of the mine floor is known also. This is not the case with ranging drum machines since the mine roof and floor are formed by separate cutting stages.

An object of the present invention is to provide a method of steering a ranging drum machine.

Accordingly, one aspect of the present invention provides a method of steering mineral cutter means which win a strip of mineral by separate roof and floor cutting stages, wherein the cutting horizon or rock boundary associated with one of the cutting stages is sensed to control the cutting horizon associated with the other cutting stage.

Conveniently, the invention provides a method wherein the cutting horizon or rock boundary associated with one of the cutting stages is sensed to control the cutting horizons associated with both the roof and floor cutting stages.

According to another aspect of the present invention, apparatus is provided for carrying out the above defined method of steering mineral cutting means, comprising means for sensing the cutting horizon or rock boundary associated with one of the cutting stages and for deriving a signal indicative of the sensed position of the cutting horizon within the mineral or of the rock boundary, and control means for controlling the cutting horizon associated with the other cutting stage in response to the signal.

Conveniently, the invention provides apparatus in which the control means controls the cutting horizons associated with both the cutting stages.

The invention also provides in combination, apparatus as defined above with a mineral mining machine provided with cutter means.

Preferably, the mining machine comprises a single rotary cutter drum carried on a ranging arm.

Alternatively, the mining machine comprises at least two rotary cutter drums carried on ranging arms, respectively.

Conveniently, the said means comprises a nucleonic detector.

Advantageously, the said means comprises a source of nucleonic radiation.

By way of example only, three embodiments of the present invention will be described with reference to the schematic accompanying drawings in which:

FIG. 1 is a diagram of a mining machine having cutter means in one operational position;

FIG. 2 is a diagram of the mining machine of FIG. 1 in another operational position;

FIG. 6 is a diagram of a mining machine similar to that of FIG. 1 but using an alternative operational procedure;

FIG. 7 is a diagram of the mining machine of FIG. 6 in another operational position.

Figure 3:
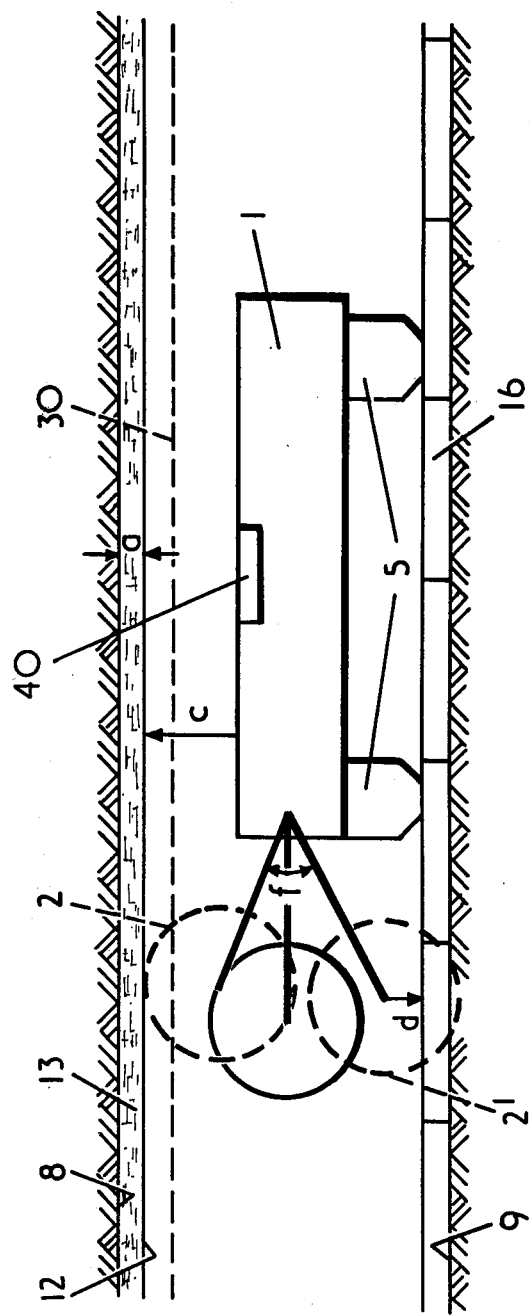
FIG. 3 is a diagrammatic side view of the machine of FIG. 1 illustrating some of the parameters which are sensed to steer the machine's cutter means.

Referring to FIGS. 1 and 2 of the drawings, the mining machine 1 is of the kind commonly known as a single ended ranging drum shearer comprising a single rotary cutter drum 2 supported by an arm pivotally mounted on the body of the machine for movement about a substantially horizontal axis. Movement of the arm 3 about its axis is controlled by a hydraulic ram (not shown).

The machine 1 has shoes 5 which slidably engage the upper flanges of an armoured face conveyor 6 extending along a working face formed in a coal seam 7 having upper and lower rock boundaries 8 and 9, respectively. The machine 1 hauls itself along a stationary haulage chain (not shown) anchored at the ends of the working face.

In operation, the machine traverses to and fro along the working face winning successive strips of mineral from the face every two traverses. The machine wins each strip of mineral by separate roof and floor cutting stages. First the machine traverses along the working face in the direction indicated by arrow A in FIG. 1 with the cutter drum 2 in its raised position so that the cutting horizon 11 associated with roof cutting stage is adjacent to the mine roof 12. A narrow band of coal 13 is left between the mine roof 12 and the upper rock boundary 8. During the whole of the machine's traverse in this direction the arm 3 is locked in position relative to the machine body.

When the machine reaches the end of the traverse the arm 3 is moved about its pivot mounting until the cutter drum is in its lower position, indicated by 2' in FIG. 2. The machine then traverses the working face in the opposite direction as indicated by arrow B in FIG. 2 so that the cutting horizon 16 associated with the floor cutting stage is adjacent to the mine floor which is shown coincident with the lower rock boundary 9. When the machine reaches the end of the traverse the machine together with the conveyor is advanced towards the working face until the cutter drum is advanced into the mineral to the desired depth. The operational procedure is then repeated with the cutter drum in its raised position as seen in FIG. 1.

Thus, successive strips of mineral are won from the working face.

During the floor cutting stage, a nucleonic sensing and detecting probe 20 is provided on the machine to sense the cutting horizon associated with the roof cutting stage. The probe is urged into contact with the mine roof 12 by a support mounting 22 which may be a telescopic arm having an adjustable length or a hinged arm which is pivoted towards the mine roof.

Figure 4:
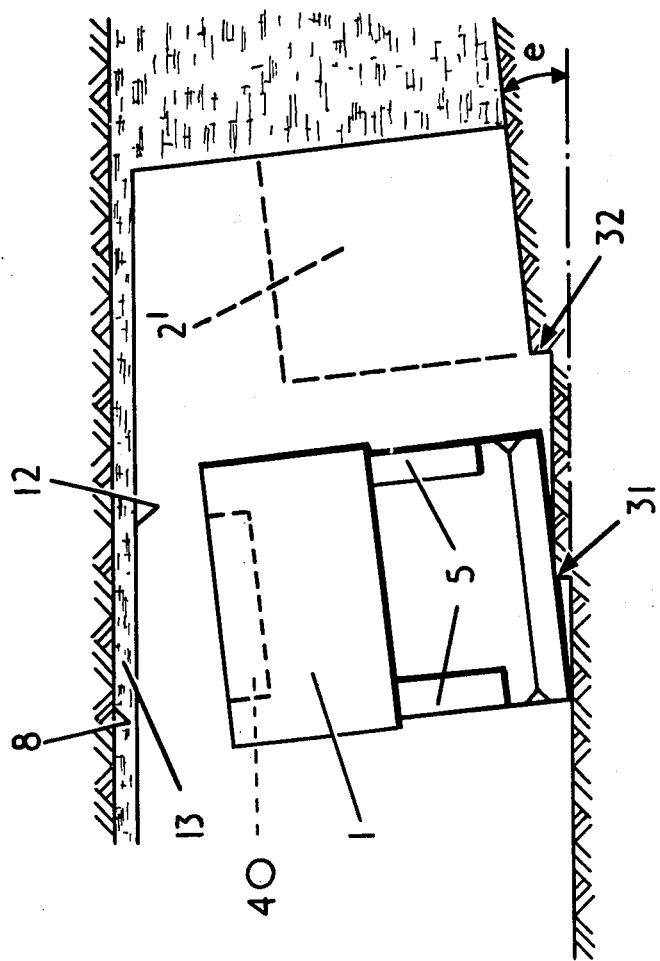
FIG. 4 is a diagrammatic cross-section of the mining machine in the operational position shown in FIG. 3 illustrating another of the parameters which is sensed to steer the machine's cutter means.
Figure 5:
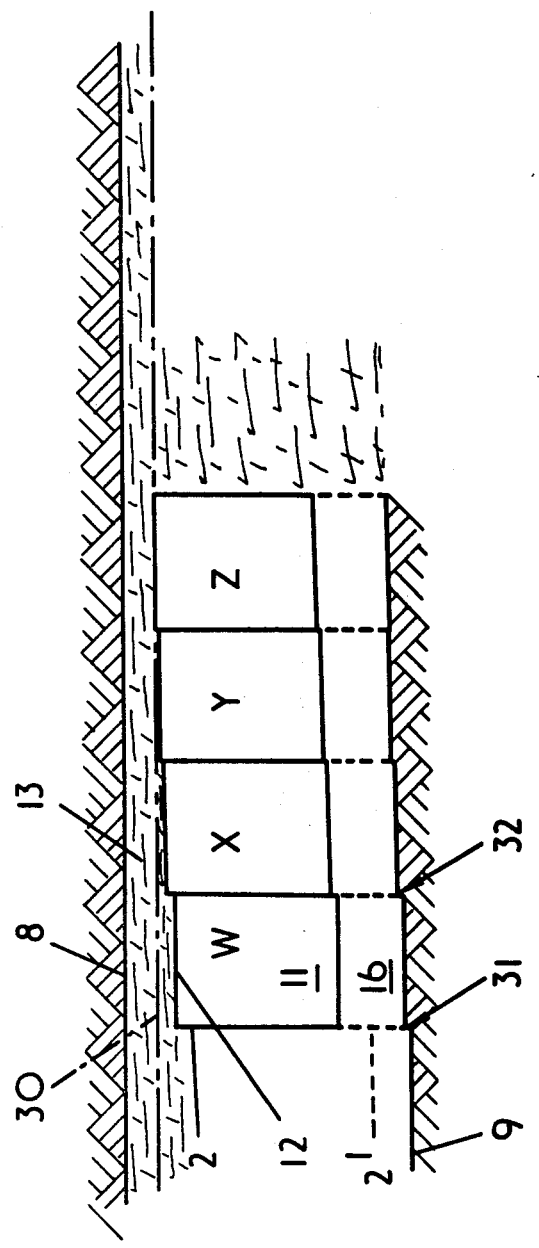
FIG. 5 is a diagrammatic cross-section through the cutter means of FIGS. 1 and 2, the cutter means being illustrated in a series of positions associated with the advance of the working face.

As the machine traverses along the working face the sensed parameters (which are discussed later in this specification) are used to control the cutting horizon 16 associated with the floor cutting stage. Thus, for example, if the probe 20 senses that the coal band 13 is too thick, a signal indicative of the excess thickness is fed from the probe to control means 40 on the machine which adjust the position of the arm 3' to raise the cutter drum by an appropriate amount relative to the conveyor. This raises the position of the mine floor relative to the conveyor so that when the conveyor 6 is advanced towards the working face into the track formed by the most recent extraction of a strip of mineral, the section of the conveyor adjacent to the portion of the coal band which was sensed as too thick moves onto the raised portion of the mine floor. Thus, the section of the conveyor associated with the raised mine floor is itself raised relative to the mineral seam so that when the machine next traverses the working face with the cutter drum in its locked raised position it forms a mine roof which is raised relative to the mineral seam and so the thickness of the band of coal 13 is correspondingly reduced. In order to avoid steps in the floor which are too great to be easily negotiated by the advancing conveyor the control means 40 are set to restrict the adjustment of the position of the cutter head relative to the conveyor position. Thus in order to obtain a band of roof coal having a desired thickness it may be necessary to make steering adjustments during a series of floor cutting stages as the machine wins successive strips of mineral. FIG. 5 shows the cutting horizon of the cutter drum in position 2 and 2' associated with the roof and floor cutting stages, respectively, for four successive strips W, X, Y and Z. During the first won strip W the cutting horizon 11 is too low relative to the mineral seam and so a roof coal band 13 is left which is thicker than the preselected value indicated by the reference horizon 30. When the machine traverses back along the working face in the floor cutting stage, the cutter drum 2' is raised when the probe 20 senses the roof band is too thick and a step 31 is formed in the mine floor, relative to the conveyor. The conveyor is advanced over the step 31 onto the raised mine floor where it takes up an inclined position as indicated in FIG. 4. When the machine next traverses along the working face to win strip X with the cutter drum 2 locked in its raised position the cutting horizon associated with the roof cutting stage is raised relative to the mineral seam towards the reference horizon 30. If the coal band thickness is still above the preselected value, the cutter drum 2' may be correspondingly raised on strip X and a further step 32 is formed in the mine floor. However, because the conveyor is inclined as shown in FIG. 4 the cutter drum 2 is also inclined upwards and therefore, reduces the thickness of the coal band 13 without raising the arm 3. The operational procedure is repeated for strips Y and Z until the roof cutting horizon is at a desired level relative to the mineral seam and a roof coal band having the desired preselected thickness is formed.

In order to successfully steer the ranging drum machine it is necessary to sense several parameters and to control the steering in accordance with the sensed parameters. FIGS. 3 and 4 indicate some of the parameters which are sensed. The parameters may include the following:

(a) The thickness of roof coal band 13 left between the mine roof 12 and the upper rock boundary 8.

In the embodiment described this parameter is sensed by the nucleonic sensing and detecting probe 20 which emits nucleonic radiation towards the rock boundary 8 and which senses the thickness of the coal band 13 by measuring the radiation backscatter. The probe 20 feeds a signal indicative of the coal band thickness to control means 40 located in the machine body.

In a modification of the apparatus, the probe may sense the mine floor.

In alternative embodiments, the cutting horizon may be sensed by detecting the natural radiation from the strata. Alternatively, a cutting force detector may be mounted on the cutter drum, the detector sensing the cutting horizon by identifying bands within the mineral seam relative to boundaries of the seam or the adjacent boundaries of the mineral seam.

Where the mine roof is coincident with the upper rock boundary as where the band 13 of roof coal falls, a roof follower may sense the mine roof.

(b) The position of the machine along the working face.

(This parameter is not indicated on FIG. 3 or 4).

The position of the machine along the working face may be sensed by counting the number of revolutions of a haulage sprocket on the machine. Alternatively, means may be provided along the working face which sense the position of the machine along the face.

(c) The position of the mine roof 12 associated with the roof cutting stage with respect to the top of the machine and therefore with respect to the conveyor.

This can be sensed by having the probe 20 mounted on a telescopic arm or on an arm hinged to the machine body, the arrangement being such that the probe 20 is urged towards the mine roof.

(d) The position of the cutter drum 2' during the floor cutting stage with respect to the conveyor.

This may be sensed by a telescopic arm from the drum to the conveyor.

(e) The inclination of the machine in a direction normal to the conveyor i.e. in the direction of working face advance.

This parameter is sensed by having an inclinometer mounted on the machine body.

(f) The position of the cutter drum 2' with respect to the machine.

This parameter is sensed by having means on the machine body which measure the angle of the arm 3' to the machine body.

Signals are derived from the sensing means which are indicative of the sensed parameters (a) to (f), the signal being fed to the control means which control the machine's steering mechanism in accordance with the received signals to maintain the machine along the preselected path within the mineral seam.

The control means 40 may comprise an analogue computer which processes the information or received signals by a prescribed formula and action is taken immediately as a result of the processing. Alternatively, the control means 40 may comprise a digital computer which stores the information or received signal and which draws on the stored information when required to take appropriate action. This latter control means has the advantage that additional information may be fed into the computer's memory and the machine steered according to the information. For example, information of known or estimated changes of the mineral seam gradient may be fed to the computer which will then take these changes into account when steering the machine.

From the above description it can be seen that the method of steering the mining machine, comprises sensing the cutting horizon associated with the roof cutting stage and controlling the cutting horizon associated with the floor cutting stage.

In the modified arrangement as illustrated in FIGS. 6 and 7, the mining machine is again a single ended ranging drum shearer 101 having a single rotary cutter drum 102 mounted on a ranging arm 103. As with the previous arrangement, the machine first wins coal from adjacent the upper rock boundary 108 leaving a coal band 113 and forming a mine roof 112. However, in this arrangement the upper coal is won with the cutter drum 102 leading the machine, the cutting direction being indicated by arrow C in FIG. 6. The lower coal is won by the cutter drum 102' in its lower position with the cutter drum trailing the machine, the cutting direction being indicated by arrow D in FIG. 7.

When this operational procedure is adopted it is possible for the probe 120 mounted on the arm 122 to sense the cutting horizon 111 associated with the roof cutting stage during both directions of traverse of the machine along the working face and to feed signals to control means 140. However, the cutting horizon 116 associated with the floor cutting stage will still be controlled by sensing the cutting horizons 111 associated with the roof cutting stage.

Figure 8:
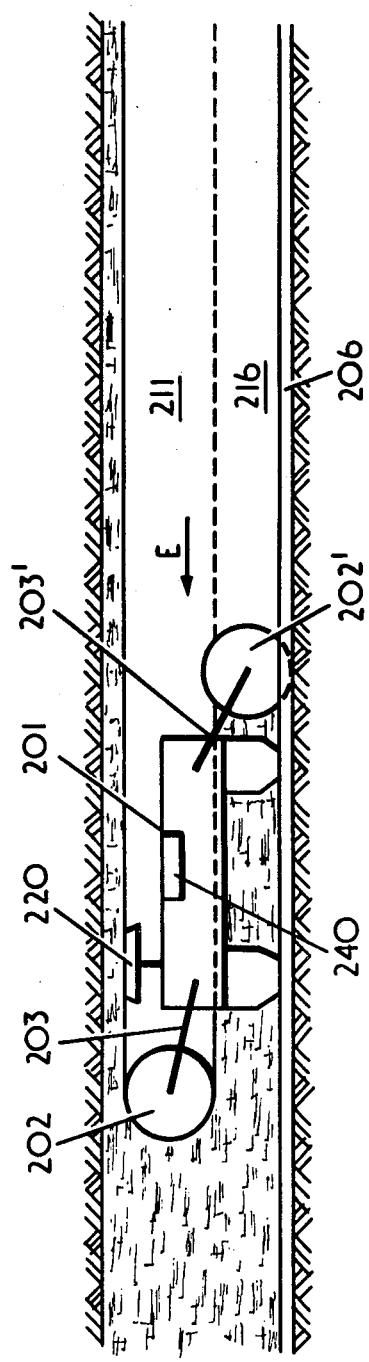
FIG. 8 is a diagram of a second embodiment of a mining machine in an operational position.

Referring now to FIG. 8, this shows a double ended ranging drum shearer 201 having two cutter drums 202 and 202' carried on arms 203 and 203' extending from opposite ends of the machine body, respectively.

The machine is shown traversing along the working face in the direction indicated by arrow E with the leading cutter drum 202 winning the upper coal and the trailing drum 202' winning lower coal. The probe 220 senses the cutting horizon 211 associated with the roof cutting stage and feeds signals to control means 240, and the cutting horizon 216 associated with the floor cutting stage is controlled by signals indicative of the sensed cutting horizon 211.

The control means 240 is similar to those described with reference to the first embodiment, the cutting horizon 216 associated with the floor cutting stage being controlled with the aid of a probe sensing the cutting horizon 211 of the roof cutting stage.

When the machine reaches the end of its traverse the position of the drums is reversed so that the drum 202 wins the lower coal and the drums are reversed so that the drum 202 wins the lower coal and the drum 202' wins the upper coal. The conveyor 206 is advanced towards the working face into the recently won track and the machine traverses along the face in the opposite direction to arrow E.

From the above description it can be seen that the present invention provides a method for steering a ranging drum machine.

In modifications of the invention described with reference to FIG. 8 of the drawings two probes are provided associated with the two drums 202, 202', respectively.

I claim:

1. In a method of steering mineral cutter means having at least one ranging drum which wins a single strip of mineral by separate roof and floor cutting stages during at least one traverse along the working face of the mineral, the improvement comprising:

traversing the working face of the mineral in a first cutting stage with a mineral cutter means having a single ranging drum;

sensing at least during a second cutting stage with nucleonic detecting means the rock boundary or related cutting horizon associated with the first cutting stage;

receiving a signal from the detecting means at least during the second cutting stage indicative of the sensed position of the rock boundary or related cutting horizon of the first cutting stage;

traversing the working face of the mineral in the second cutting stage with the mineral cutter means;

controlling the height of the cutting horizon of the second cutting stage by adjusting it in response to said signal; and advancing the mineral cutter means forward into the working face of the mineral subsequent to the winning of the strip of mineral, whereby the mineral cutter means may be steered along a predetermined path within a mineral seam.

2. A method as claimed in claim 14, wherein the cutting horizon or rock boundary associated with one of the cutting stages is sensed to control the cutting horizons associated with both the roof and floor cutting stages.

3. Apparatus for steering mineral cutter means which win a strip of mineral by separate roof and floor cutting stages, in which the cutting horizon or rock boundary associated with one of the cutting stages is sensed to control the cutting horizon associated with the other cutting stage, comprising means for sensing the cutting horizon or rock boundary associated with one of the cutting stages and for deriving a signal indicative of the sensed portion of the cutting horizon within the mineral or of the rock boundary, and control means for controlling the cutting horizon associated with the other cutting stage in response to the signal.

4. Apparatus as claimed in claim 3, in which the control means controls the cutting horizons associated with both the cutting stages.

5. Apparatus according to claim 4, in combination with a mineral mining machine provided with cutter means.

6. Apparatus according to claim 5, in which the mining machine comprises at least two rotary cutter drums carried on ranging arms, respectively.

7. Apparatus according to claim 3 in combination with a mineral mining machine provided with cutter means.

8. Apparatus according to claim 7, in which the mining machine comprises a single rotary cutter drum carried on a ranging arm.

9. Apparatus according to claim 7, in which the mining machine comprises at least two rotary cutter drums carried on ranging arms, respectively.

10. Apparatus for sensing with a sensing means the cutting horizon or rock boundary after the first stage cut and adjusting the depth of the second cut in response to the sensing means, comprising nucleonic detector means for sensing the cutting horizon or rock boundary associated with the first cutting stage and for deriving a signal indicative of the sensed position of the cutting horizon within the mineral or of the rock boundary, and control means for controlling the cutting horizon associated with the second cutting stage in response to the signal.

11. Apparatus according to claim 10, comprising source means of nucleonic radiation.

12. Apparatus according to claim 10, in which the control means controls the cutting horizons associated with both the roof and floor cutting stages.

13. Apparatus according to claim 11, comprising source means of nucleonic radiation.

14. In a method of steering mineral cutter means having at least one ranging drum which wins a single strip of mineral by separate roof and floor cutting stages during at least one traverse along the working face of the mineral, the improvement comprising:
   traversing the working face of the mineral with a simultaneous first and second cutting stage by a mineral cutter means having two ranging drums;
   sensing with nucleonic detecting means the rock boundary or related cutting horizon associated with one of said first and second cutting stages;
   receiving a signal from the detecting means indicative of the sensed position of the rock boundary or related cutting horizon of the sensed cutting stage;
   controlling the height of the cutting horizon of the other of said first and second cutting stages by adjusting it in response to said signal; and
   advancing the mineral cutter means forward into the working face of the mineral subsequent to the winning of the strip of mineral, whereby the mineral cutter means may be steered along a predetermined path within a mineral seam.

15. A method as claimed in claim 14, wherein the cutting horizon or rock boundary associated with one of the cutting stages is sensed to control the cutting horizons associated with both the roof and floor cutting stages.

16. Apparatus for steering a single ranging drum mineral cutter means which wins a single strip of mineral by separate roof and floor cutting stages during two passes along the working face of the mineral in which the rock boundary or related cutting horizon associated with one of the cutting stages is sensed to control the cutting horizon associated with a subsequent cutting stage, comprising:
   a mineral cutter comprised of a single ranging cutter drum;
   nucleonic detecting means extending from said mineral cutter for sensing the rock boundary or related cutting horizon associated with the first of the cutting stages for deriving a signal indicative of the sensed position of the rock boundary or related cutting horizon within the mineral; receiving means for receiving a signal from the detecting means indicative of the sensed position of the rock boundary or related cutting horizon of the first cutting stage; and
   control means for controlling the height of the cutting horizon of a second cutting stage in response to the signal, whereby the mineral cutting means may be steered along a predetermined path within a mineral seam.

17. Apparatus for steering a double ranging drum mineral cutter means which wins a single strip of mineral by separate roof and floor cutting stages during a single pass along the working face of the mineral in which the rock boundary or related cutting horizon associated with one of the cutting stages is sensed to control the cutting horizon associated with the other cutting stage, comprising:
   a mineral cutter comprised of double ranging cutter drums;
   nucleonic detecting means extending from said mineral cutter for sensing the rock boundary or related cutting horizon associated with one of the cutting stages and for deriving a signal indicative of the sensed position of the rock boundary or related cutting horizon within the mineral;
   receiving means for receiving a signal from the detecting means indicative of the sensed position of the rock boundary or related cutting horizon of the first cutting stage; and
   control means for controlling the height of the cutting horizon of a second cutting stage in response to the signal, whereby the mineral cutter means may be steered along a predetermined path within a mineral seam.

18. A method of controlling a cutting horizon of mineral cutter means which win a strip of mineral by separate roof and floor cutting stages comprising:
   (a) cutting one of the separate roof and floor stages;
   (b) cutting the other of the separate roof and floor stages;
   (c) controlling the cutting horizon of one of said cutting stages by sensing the cutting horizon associated with the other cutting stage.

* * * * *